(12) United States Patent
Brunt et al.

(10) Patent No.: US 6,444,726 B1
(45) Date of Patent: Sep. 3, 2002

(54) BIOCIDAL COMPOSITIONS

(75) Inventors: Keith D Brunt, Nottinghamshire; Richard J Corbett, Derbyshire; Philip N Wood, Bedfordshire; Dennis Murphy, Suffolk, all of (GB)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 08/615,423

(22) Filed: Mar. 14, 1996

(30) Foreign Application Priority Data

Mar. 14, 1995 (GB) .............................. 9505083

(51) Int. Cl.$^7$ .......................... A61K 33/38; A01N 59/16
(52) U.S. Cl. ...................... 523/122; 424/405; 424/409; 424/618; 524/423
(58) Field of Search .................... 523/122; 424/409, 424/421, 618, 405; 524/403

(56) References Cited

U.S. PATENT DOCUMENTS

| | | | | |
|---|---|---|---|---|
| 4,031,055 A | * | 6/1977 | Dupont et al. ............... | 523/122 |
| 4,396,413 A | * | 8/1983 | Miller et al. ................. | 514/189 |
| 4,938,958 A | * | 7/1990 | Niira .......................... | 523/122 |
| 5,180,585 A | | 1/1993 | Jacobson et al. ............ | 424/405 |
| 5,413,788 A | * | 5/1995 | Edwards et al. ............ | 424/618 |
| 5,470,585 A | * | 11/1995 | Gilchrist ..................... | 424/409 |
| 5,595,788 A | * | 1/1997 | Jacobson et al. ........... | 424/421 |

FOREIGN PATENT DOCUMENTS

| | | | | |
|---|---|---|---|---|
| EP | 0 251 783 | | 1/1988 | .......... A01N/59/16 |
| EP | 0 427 858 A1 | | 5/1991 | .......... A01N/25/08 |
| EP | 0 444 939 A1 | | 9/1991 | .......... A01N/59/20 |
| JP | 0136507 | * | 7/1985 | ................. 424/130 |
| WO | WO 95/10940 | | 4/1995 | .......... A01N/59/16 |

OTHER PUBLICATIONS

Database WPI, Section Ch. Week 9245, Derwent Pub. Ltd., London, GB, AN 92–368625, XP 002048413 (09/92).

* cited by examiner

*Primary Examiner*—Peter Szekely
(74) *Attorney, Agent, or Firm*—Pillsbury Winthrop LLP

(57) ABSTRACT

A composition, eg a water-based polymer emulsion, cosmetics and the like, is preserved against microorganism growth, by incorporation of from 5–1000 ppm of an inorganic biocidal component which comprises a sparingly soluble silver compound deposited on a synthetic oxidic support.

15 Claims, No Drawings

BIOCIDAL COMPOSITIONS

The present invention concerns biocidal compositions. More especially, it concerns compositions comprising a silver compound supported on an oxidic support.

Many proposals have been made to utilise the antimicrobial action of silver and silver compounds since the Romans discovered the bactericidal or bacteriostatic properties of silver drinking vessels. We have previously described (EP 251 783 A) an antimicrobial composition comprising an antimicrobial silver compound deposited on an inert oxidic support The preferred composition is described as AgCl deposited on a support such as titania. The silver compound is deposited at a loading of 1–75% by weight of the support material, particularly at a loading of 15–25% by weight, that is, 0.99%–42.9% silver compound on the basis of the composite itself and assuming that the silver species is silver chloride. This antimicrobial material has been marketed and sold under the trade mark "JMAC".

JP 2-268103 (Kanebo and Tanaka) is a later disclosure of similar materials.

The said EP 251 783 teaches the use of the antimicrobial material as a component of a coating system, particularly for medical devices such as catheters, or for impregnating plastics objects. EP 251 783 teaches that the antimicrobial material is to be incorporated into a polymer in an amount of 5–60% by wt. Furthermore, it teaches the use of the composition to provide an antimicrobial effect into the environment encountered during use, and not primarily as protection of the device or composition into which it is incorporated from the environment itself, although the levels of material to provide the duty required will certainly protect the system from the environment.

We have now discovered that compositions comprising the JMAC product, show a surprising activity as biocidal and/or preservative components in a variety of materials, at concentrations very much lower than those previously recommended.

The present invention provides a composition protected against microorganism growth, especially against bacteria, yeasts and moulds, comprising a biocidal component which is a sparingly soluble silver compound deposited on a synthetic oxidic support at a loading of 1–75% by weight of the support, characterised in that said biocidal component is dispersed in said composition in an amount of from 5–1,000 ppm based on the total weight of the composition.

The actual concentration of the biocidal component depends upon the nature of the major component of the composition, and may be determined by routine testing. In some preferred embodiments of the present invention, concentrations are from 10–600 ppm, for example from 10–50 ppm of the biocidal component The biocidal component is conveniently that marketed by Johnson Matthey PLC as "JMAC", but may be any similar material. Preferred silver compounds are silver chloride, although silver iodide, phosphate, hydroxide, carbonate, bromide, acetate, citrate, lactate, salicylate and stearate, as well as mixtures thereof with one another or with other silver compounds may be used. Preferred supports are titania and other stable oxidic supports comprising an oxide or hydroxide or comprising an oxy-anion species such as phosphate or sulphate. The biocidal component of the invention may be prepared in the same manner as described in the above-mentioned EP 251 783.

The solubilities of the silver compounds referred to above are shown below in Table I:

| Compound | Temp ° C. | Solubility g/l |
|---|---|---|
| Silver Chloride | 25 | 0.00193 |
| Silver Iodide | 25 | 0.0000026 |
| Silver Phosphate | 20 | 0.00644 |
| Silver Stearate | 20 | 0.00065 |
| Silver Bromide | 25 | 0.000135 |
| Silver Oxide (hydroxide) | 25 | 0.00020 |
| Silver Acetate | 25 | 11.11 |
| Silver Carbonate | 25 | 0.033 |
| Silver Citrate | 25 | 0.0284 |
| Silver Salicylate | 23 | 0.95 |
| Silver Lactate | No Data | |

The above data was obtained from "Solubilities of Organic & Inorganic Compounds", Vol. 1, $4^{th}$ Ed. By Stedel (Publisher: C. Van Nostrand).

The biocidal composition may usefully be surface modified, that is, surface coated or treated to provide desired physical and/or chemical properties to improve performance in the composition. For example, the biocidal component may be surface coated with a polymer such as PVA, PEG or PVP to provide a chemical and/or physical pathway for silver.

The composition of the invention may incorporate one or more diluents, adjuvants or other components, eg odour control substances, colouring or thickening substances and the like, that either have no substantial adverse effect on the biocidal properties of the silver containing component or have a beneficial effect. For example, other biocides may be incorporated, or a surfactant. It has been found that certain surfactants have a particularly and unexpectedly beneficial effect on the preservative properties of the biocidal component. An especially preferred surfactant is sodium dioctyl sulphosuccinate (hereinafter called "DOSS"), which may be purchased from a variety of sources. This substance is reported to have slight bactericidal properties and to enhance the activity of phenolic and mercurial disinfectants, but appears to show a remarkable synergy with the silver-containing biocidal component. One of the properties of DOSS is to act as a thickener, in general, we have found that most alternative thickeners, including the commonly used xanthate gums, tend to adversely affect the silver-containing biocidal component.

In a preferred embodiment, the biocidal component is suspended in a concentrate composition, eg containing 1–15 wt. % of biocidal component, together with about 15 wt. % of a DOSS solution, the balance being water. The DOSS solution may be in a glycol solvent, but other solvents, including alcohols, such as isopropyl alcohol or ethanol, may be used. For example, the DOSS may be present as a 60–70% by weight concentration in an alcohol/water or glycol/water mixture. Such a concentrate composition forms a part of the present invention. The concentrate composition is then available for dispersing into the final composition, at the desired concentration.

Another suitable concentrate composition according to the invention is an emulsion, either of the water-in-oil or the oil-in-water type, in which the biocidal component is dispersed in one of the phases. The emulsion can then, in turn, be dispersed into the desired material to be preserved. It may be appropriate, for some materials, for the emulsion to be broken at this stage.

The biocidal component is remarkably non-toxic for higher life forms, whilst being efficacious against a wide variety of micro-organisms, including bacteria, yeasts and moulds. This permits safe handling of the concentrate without excessive precautions, and demonstrates a remarkable contrast to prior existing preservatives in the art, which are all toxic organic compounds. The biocidal component remains effective at, on average, significantly lower concentrations in the final composition than most organic preservatives; the few organic preservatives that are effective at or around 5 ppm are extremely toxic in concentrated form.

The preserved compositions may be primarily a polymer or polymer solution or emulsion, for example a natural or synthetic latex, which may be intended for foaming to form a carpet backing, for coating or finishing fibres, fabrics or papers. The biocidal component may be incorporated into steam vulcanised latexes.

Other compositions of particular interest, and in which the biocidal component is effective, are cosmetics, both "leave on" and "rinse off" type cosmetics, which can be subject to undesired bacterial growth, shampoos, sun-screens, water-based adhesives and paints, and detergent systems or liquid soaps. The composition may be, in a particular embodiment, a printing ink (whether or not pigmented) which may be printed or coated onto paper or plastics film packaging, for example to form a food packaging which inhibits microorganism growth at the interface between the packaging and a food product.

In another embodiment of the invention, the biocidal component is incorporated into a moulding, extruding or spinning plastics or polymeric composition, in sintered, foamed or blown compositions, in an amount of up to 0.1% by wt; this is very much lower quantity than that taught in the EP 251 783 of 5 to 60 wt. %, exemplified by a 15–40 wt. % concentration for a 20% AgCl on $TiO_2$ biocidal component.

To demonstrate the synergistic effect of the combination of commercial JMAC powder (20% silver chloride, 80% titanium dioxide) and DOSS, tests were carried out to compare the Minimum Inhibitory Concentration (MIC) of the powder as a dry solid (product 1), a combination of JMAC and DOSS (10% JMAC powder, 9% DOSS, 2.25% alcohol and 78.75% water—product 2), a concentrate composition according to the invention, and a commercial DOSS solution (70% DOSS, 15% water and 15% polyethylene glycol—product 3), for a wide variety of microorganisms.

The results are shown below in the Table, from which it can readily be seen that although the JMAC powder (product 1) shows the lowest MIC, ie is the most potent, and the DOSS solution (product 3) has relatively little potency, the JMAC+DOSS mixture (product 2) is surprisingly effective given that the concentration of JMAC powder is only 10% of product 1. That is, the actual concentration of biocidal silver is much reduced in product 2 and a MIC of 400 becomes the equivalent to 40 ppm of JMAC powder (product 1). This 10-fold equivalent reduction is shown in the brackets for product 2 in the Table.

TABLE II

| ORGANISM | MIC in ppm Product | | |
|---|---|---|---|
| | 1 | 2 | 3 |
| Bacteria | | | |
| S Aureus NCTC 10788 | 160 | 400 (40) | 8000 |
| S edidermis biotype 3 | 160 | 400 (40) | 4000 |
| Lactobacillus buchneri | 160 | 400 (40) | 4000 |
| PS aeuginosa NCTC 6749 | 160 | 400 (40) | 64000 |
| E coli ATCC 8739 | 160 | 400 (40) | 32000 |

TABLE II-continued

| ORGANISM | MIC in ppm Product | | |
|---|---|---|---|
| | 1 | 2 | 3 |
| Klebsiella pneumoniae ATCC 13315 | 160 | 400 (40) | 32000 |
| Serratia marcescens NCTC 1377 | 160 | 400 (40) | 16000 |
| Listeria monocytogenes NCTC 10357 | 160 | 400 (40) | 4000 |
| B subtilis NCTC 3160 | 160 | 400 (40) | 8000 |
| B cereus NCTC 7464 | 160 | 400 (40) | 32000 |
| Yeasts | | | |
| C albicans NCYC 597 | 160 | 400 (40) | — |
| C albicans NCPF 3179 | 160 | 400 (40) | 1000 |
| C parapsilosis | 160 | 400 (40) | — |
| C bordinii | 160 | 400 (40) | 16000 |
| Sacc cerevisiae NCYC 200 | 160 | 400 (40) | 16000 |
| Sacc rouxii NCYC 381 | 160 | 400 (40) | 16000 |
| Pink yeast | 80 | 400 (40) | — |
| Oidium sp | 80 | 400 (40) | 16000 |
| Moulds | | | |
| Aspergillus flavus | >160 | — | 16000 |
| Aspergillus fumigatus IMI 134735 | >160 | — | 4000 |
| Aspergillus niger IMI 17454 | 160 | 1600 (160) | 8000 |
| Aspergillus glaucus | 160 | 400 (40) | 8000 |
| Moulds | | | |
| Penicillium notatum | >160 | 400 (40) | 4000 |
| Cladosporium herbarum | >160 | 400 (40) | 4000 |
| Trichothecium ciride | >160 | 400 (40) | 4000 |
| Acternaria alternata | >160 | 400 (40) | 16000 |
| Myrothecium verruccaria | >160 | 400 (40) | 16000 |
| Verticillium psalliotae | >160 | 400 (40) | 8000 |

The invention will now be described with reference to the following examples of compositions according to the invention.

EXAMPLE 1

100 g of commercial JMAC powder, containing 20% AgCl on titania, was mixed with 150 g of DOSS in 70% mixture by vol in propylene glycol/water, and the mixture diluted with 750 g water.

A concentrate suspension was obtained which is safe to handle, being non-irritant and non-sensitising to healthy human skin.

The concentrate was admixed, in an amount of 20 ppm, with a commercial leave-on facial cream. The final composition retained its colour and "feel" and was preserved, as tested by an established BP protocol, against challenge by a variety of microorganisms.

EXAMPLE 2

The concentrate of Example 1 was added, at a concentration of 600 ppm, to a commercial water-based white emulsion paint. No colour change could be detected. The paint was preserved against microorganism growth when challenged with a variety of moulds.

We claim:

1. A concentrate biocidal composition comprising a synergistic combination of (i) 1–15 wt. % of a biocidal silver compound deposited on a synthetic oxide support and (ii) about 15 wt. % of sodium dioctyl sulphosuccinate, the balance of said composition consisting essentially of water.

2. A biocidal composition comprising a synergistic combination of (i) a biocidal silver compound deposited on a synthetic oxide support at a loading of 1 to 75% by weight of the support and (ii) a sulphosuccinate.

3. A concentrate biocidal formulation comprising a synergistic combination of (i) a biocidal component and (ii) a sulphosuccinate compound, in water, wherein the biocidal component is a silver compound having a solubility of up to and including 11.11 grams per liter deposited on a synthetic oxide support at a loading of 1 to 75% by weight of the support.

4. A concentrate biocidal formulation according to claim 3 which comprises 1–15 wt. % of the biocidal component.

5. A concentrate biocidal formulation according to claim 3 which comprises approximately 15 wt. % of the sulphosuccinate compound.

6. A concentrate formulation according to claim 3 wherein the silver compound has a solubility up to and including 0.95 grams per liter.

7. A concentrate formulation according to claim 3 wherein the sulphosuccinate compound is sodium dioctyl sulphosuccinate.

8. A composition protected against microorganism growth, comprising a substance which is normally subject to undesired microorganism growth, said substance having added thereto an effective amount of a biocidal formulation according to claim 2 wherein the final concentration of biocidal component (i) in the protected composition is from 5–1000 ppm based upon the total weight of the protected composition.

9. A composition according to claim 8 wherein the final concentration of biocidal component in the composition is from 5–600 ppm.

10. A composition according to claim 9 wherein the final concentration of biocidal component in the composition is from 10–50 ppm.

11. A composition according to claim 8 wherein the composition is a leave-on or rinse-off cosmetic.

12. A composition according to claim 8 wherein the composition is a water-based polymer emulsion.

13. A composition according to claim 8 wherein the composition is a plastics or polymeric composition.

14. A composition according to claim 8 wherein the biocidal component is silver chloride deposited on titania.

15. The method of protecting an object against microorganism growth which comprises applying to said object an effective amount of biocidal composition according to claim 2.

* * * * *